United States Patent [19]

Matzinger et al.

[11] Patent Number: 5,187,100
[45] Date of Patent: Feb. 16, 1993

[54] DISPERSION TO LIMIT PENETRATION OF AQUEOUS SOLUTIONS INTO A MEMBRANE

[75] Inventors: David P. Matzinger, Menlo Park; Maria Teodorczyk, Palo Alto; Darwin R. Poulos, Los Altos, all of Calif.

[73] Assignee: Lifescan, Inc., Mountain View, Calif.

[21] Appl. No.: 795,285

[22] Filed: Nov. 19, 1991

Related U.S. Application Data

[63] Continuation of Ser. No. 530,044, May 29, 1990, abandoned.

[51] Int. Cl.$^5$ ............................................. G01N 31/00
[52] U.S. Cl. ........................................ 436/16; 436/14; 435/14; 422/56; 422/61; 252/408.1; 252/352; 524/563
[58] Field of Search ........................................ 436/8-18, 436/528, 533, 534; 422/56, 61; 435/14; 252/408.1, 352; 524/563

[56] References Cited

U.S. PATENT DOCUMENTS

| | | | |
|---|---|---|---|
| 3,558,522 | 1/1971 | Louderback et al. | 436/10 |
| 4,020,006 | 4/1977 | Parker | 436/8 |
| 4,133,774 | 1/1979 | Brynko et al. | 252/62.1 |
| 4,151,108 | 4/1979 | Sorensen et al. | 436/11 |
| 4,220,698 | 9/1980 | Brynko et al. | 430/109 |
| 4,576,604 | 3/1986 | Guittard et al. | 424/473 |
| 4,729,959 | 3/1988 | Ryan | 436/14 |

Primary Examiner—Jill A. Johnston
Assistant Examiner—N. Bhat

[57] ABSTRACT

A control solution for use with a porous reagent strip comprises a flexible semisolid polymer dispersed in water, such as polyvinyl acetate in distilled water, with appropriate control glucose concentration levels. This solution is useful in mimicking whole blood in conjunction with porous reagent strips to determine compliance of the strips and meters to established measurement and performance criteria.

11 Claims, 1 Drawing Sheet

DISPERSION TO LIMIT PENETRATION OF AQUEOUS SOLUTIONS INTO A MEMBRANE

This is a continuation of application Ser. No. 07/530,044, filed May 29, 1990, now abandoned.

FIELD OF THE INVENTION

This invention relates to a dispersion for use in a membrane. More specifically, the invention relates to a dispersion used to inhibit penetration of aqueous solutions in a membrane. Most specifically, the invention relates to a dispersion to inhibit penetration of aqueous solutions in a membrane, where the dispersion is used in a control solution useful in the quality control and performance verification of glucose measuring meters and reagent strips.

BACKGROUND OF THE INVENTION

Reagent strips are quite popular for use in colorimetric reactions, in which strip color is read by a hand-held meter, specifically, reagent strips are useful in the determination of analyte levels in blood. Even more specifically, reagent strips have been useful in the determination of glucose levels in whole blood. Blood samples are placed on the reagent strip, and after reaction with components embedded in the strips, a determination of glucose levels in whole blood is made. The meter is capable of discerning information from the reaction to determine glucose levels in whole blood. Measuring meters, such as glucose measuring meters, and reagent strips, such as glucose measuring reagent strips, vary in accuracy and preciseness of measuring capabilities. It is therefore necessary to provide a monitoring agent, known as a control solution, which determines whether meters and strips are rendering meaningful descriptions of glucose levels. Of course, it is important to have this solution act in as close as possible a manner to the sample, i.e., whole blood.

In porous membrane-based reagent strips, red blood cells (erythrocytes) play an important part in controlling sample flow. When whole blood is applied to the top surface of the membrane, the liquid portion of the blood (plasma) immediately penetrates the porous structure, drawn in by capillary action. As plasma is drawn toward the surface of the membrane, it carries erythrocytes with it. When the erythrocytes contact the surface of the membrane, they are prevented from entering the membrane by pores which are smaller than the erythrocytes. The erythrocytes may rupture due to surface properties of the membrane or capillary suction, releasing their liquid contents into the membrane, but the erythrocyte cell membrane (ruptured or not) remains at the reagent membrane surface, blocking progress of plasma into the pores. When all of the surface pores are covered by erythrocytes, all flow of plasma into the reagent membrane ceases.

This flow control feature of whole blood is important for three reasons. First, if flow of plasma were to continue unimpeded, gravity would cause excess fluid to accumulate on the lower surface of the membrane where reading takes place. This excess fluid would impede accurate reflectance measurements of developed color on the reading surface. Second, continued delivery of analyte (i.e., glucose in the case of a glucose reagent strip) to the reagent system results in increasing color intensity as long as flow continues. In contrast, if plasma flow is stopped upon reaching the reading surface of the membrane, then the analyte sample size is controlled, and color variation ceases when this analyte is completely reacted. Third, in the absence of a flow controlling factor, plasma will be drawn into the membrane surrounding the sample application zone, carrying with it reagents and developed dyes, and depleting the concentration of these chemicals in the center of the zone.

Separately or in combination, the above three effects inhibit the ability of the system to reproducibly measure analyte levels in aqueous solutions. Thus, when analyte is presented in an artificial matrix (control solution), better precision is obtained if this artificial matrix possesses flow control characteristics similar to whole blood. Precision is important with control solution because typically the reagent strip/meter system is said to be functioning properly if the control solution produces a reading in a prescribed range. As the imprecision of the system increases, this range must be broadened, and the value of a single control test as an indication of system performance decreases.

Previous control solutions have attempted to mimic whole blood samples on reagent strips, but for reasons listed below, control solution reproducibility is difficult to attain. Current control solutions are made viscous by the addition of water-soluble polymers such as methyl cellulose, polyvinylpyrrolidone or hydroxypropyl cellulose. This increased viscosity greatly slows down, but does not completely eliminate the formation of excess solution on the reading surface. Thus, a viscosity-modified control solution give>better precision than an unmodified aqueous control, but does not operate as well as blood. In addition, the high viscosity necessary to significantly slow the flow makes the control solution difficult to handle during manufacture and dispensing.

SUMMARY OF THE INVENTION

It is therefore an object of the invention to provide a control solution which mimics whole blood.

It is further an object of the invention to provide a control solution which mimics the performance of whole blood on porous reagent strips by mimicking flow properties of whole blood.

It is yet another object of the invention to provide a control solution which mimics the performance of whole blood when used on porous reagent strips for testing glucose concentration levels in whole blood.

It is yet another object of the invention to provide a control solution including known levels of glucose useful with a porous reagent strip in combination with a glucose measurement meter.

It is a final object of the invention to provide a control solution which is useful over a wide range of blood glucose concentrations to mimic blood when placed on a reagent strip useful with meters for testing blood glucose levels, in order to verify compliance to performance characteristics of both reagent strip and meter.

These and other objects of the invention are achieved in a two-phase dispersion of deformable particles in an aqueous medium. The dispersion comprises particles of a non-water soluble polymer dispersed in water, coupled with controlled levels of glucose. The deformable solid particles are dispersed in water so that the bulk solution is essentially inviscid. The particles suspended in the bulk solution are prevented from coalescing in the water in which they are suspended.

It has been found that one useful combination of a polymer suspended aqueous medium where the dispersion mimics the performance of blood in reagent strips used in glucose measurements is a suspension of polyvinyl acetate particles in water. The polymer is insoluble in water, and a surfactant suspends the particles in the water to form a dispersion. Best performance is obtained in a ratio of one part 40–55% solid dispersion in six parts water. When various glucose concentration levels are added to the emulsion, the emulsion is useful in mimicking blood when placed on reagent strips for determination of glucose levels. This embodiment becomes useful as a control solution to determine compliance of porous reagent strips and meters which measure glucose.

These and other objects of the invention will be better understood by the following detailed description of the drawings in connection with the detail description of the invention .

DETAIL DESCRIPTION OF THE DRAWINGS

FIG. 1 is a perspective view of a reagent strip useful in the measuring of glucose levels in blood; and FIG. 2 is a cross sectional view of a reagent strip useful in the measurement of glucose levels in blood.

DETAILED DESCRIPTION OF THE INVENTION

Figure 1:
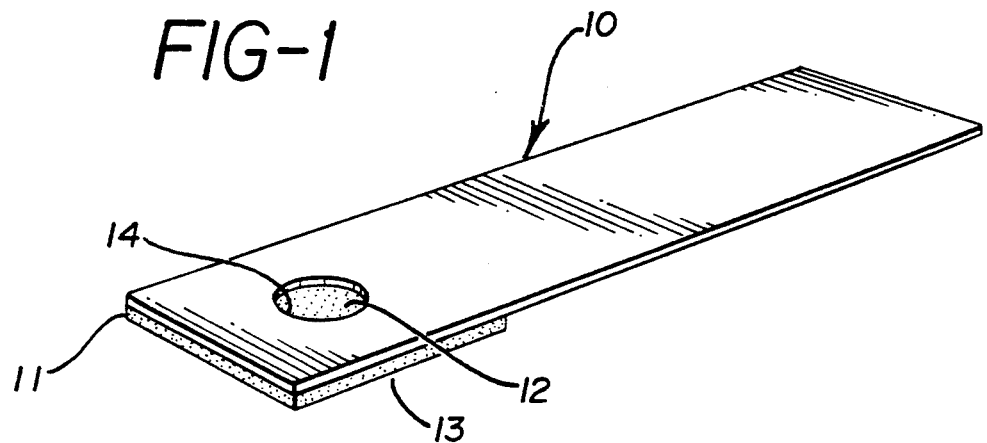
Figure 2:
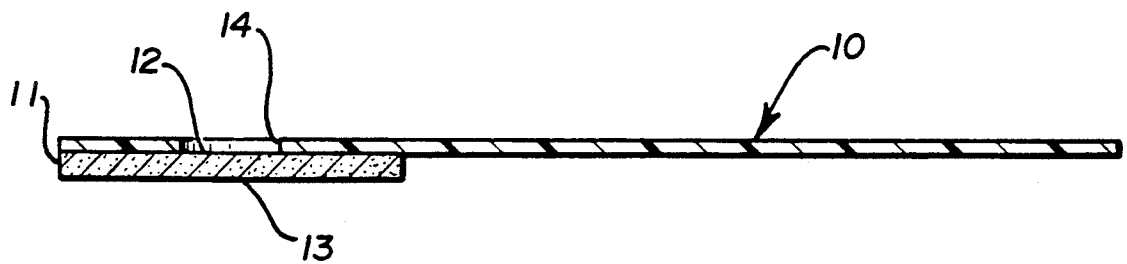

As seen in FIGS. 1 and 2, a reagent strip 10 useful in the measuring of whole blood typically will have a porous open-celled matrix 11 capable of transporting a liquid. On one side 12, a blood sample will be placed at hole 14. Blood will seep from capillary effect to the opposite side 13 of the matrix 11. Glucose in the blood reacts with reagents embedded within the matrix 11. When passing into the matrix 11, red blood cells disperse and close the pores of the matrix, so that a limited volume of liquid phase flows into the reaction zone and an accurate reflectance measurement can be made on opposite side 13.

Generally, glucose in the liquid portion of the sample then reacts to produce a colorimetric change, detectable by an optical meter into which the reagent strip 10 is placed. This optical meter will then determine levels of glucose or other analytes contained in the whole blood sample.

In order to determine whether the meters and reagent strips 10 are operating properly, it is periodically useful to test them using a control solution with a known concentration of glucose. It is this control solution formulation which is the basis of the invention.

In formulation of an appropriate control solution, many factors go into selection. Most specifically, it is desirable to obtain a control solution which accurately mimics blood on porous reagent strips. It has been found that an emulsion of semi-solid polymeric particles in an aqueous medium most accurately mimics the performance of whole blood samples on a porous glucose measuring reagent strip. In one typical measurement system, these reagent strips have a 0.8 micron pore size through which the whole blood sample seeps. It is noticed that in whole blood samples, the liquid will seep through the pores in a reagent strip of this size, and erythrocytes remain on the sample side 12 of the reagent strip 10 effectively limiting sample flow by closing the pores of the matrix 11. It is therefore desirable to create a control solution which closes pores in the reagent strip, similar to the way erythrocytes behave in whole blood.

Furthermore, it has been discovered that various polymers effectively behave like erythrocytes in whole blood, especially those "tacky" polymers containing flexible particles, as later explained.

Polyvinyl acetate having about 0.5 to 10.0 microns particle size when suspended in water almost accurately mimics these characteristics of whole blood samples. These particles of polyvinyl acetate alone form a very viscous fluid; they must be dispersed in water so that the bulk liquid solution formed from the emulsion is essentially inviscid, like blood. Ideally, these flexible, semi-solid particles remain dispersed in control solution throughout its use in mimicking a blood sample.

In control levels of 300 mg/dl glucose concentration, a polyvinyl acetate suspension commercially available as a liquid with approximately 40% to 55% solid by weight performs admirably when placed in a weight ratio of suspension to water between 1:2 and 1:10. Most specifically, ratios of about 1:5 up to about 1:6 per weight with water perform best, especially a ratio of about 1:6. This ratio provides reproducibility for glucose readings and penetration of solutions through a typical porous glucose reading membrane. With other membranes, polyvinyl acetate to water ratios would differ, and it is the intention of this invention to disclose the use of the polyvinyl acetate dispersion as a control solution for a variety of porous strips over a variety of measurement situations.

In certain glucose measuring systems, such as the One-Touch TM system manufactured by the assignee of this invention, whole blood readings are taken at 635 nm and 700 nm wavelengths. It is necessary in such a system to provide an offset adjuster which permits the system to read proper glucose levels at these wavelengths. Through experimentation, copper phthalocyanine tetrasulfonic acid tetrasodium salt performed admirably in control solution both at 0 mg/dl and 300 mg/dl glucose.

The polyvinyl acetate control solution forms a dispersion, a two-phase system in which one phase, the polyvinyl acetate particles, are distributed about the water phase. Because the particles interact with the medium, the proper level of dispersion may not necessarily be maintained. Consequently, due to the attractive force between polyvinyl acetate particles, there is a tendency for the dispersed particles to come together to form large units, unless there is a mechanism preventing such attraction of polyvinyl acetate particles.

If the polymer particles settle to the bottom of the control solution vial, the performance of the control solution lessens. In addition, resuspending particles is an additional step for the user. Thus a dispersion stabilizer is necessary to cause the system to resist forming these flocculates. It has been found that AEROSIL TM 200 comprising very fine spherical silicon dioxide particles (between 7 nm and 40 nm diameter) acts well as a dispersion stabilizer in the polyvinyl acetate emulsion, and also provides for rapid redispersion of polymer particles. Other surfactants may be useful as dispersion stabilizers, such as those surfactants which are residues of the emulsion polymerization process which forms polyvinyl acetate particles.

Initially, the bulk polyvinyl acetate emulsion has an approximate pH between 4.5 and 6.0. Ready to use control solution of the present invention has a pH of about 4.9±0.2. However, no change was noticed in control performance within a pH between about 3.5 to about 5.9.

EXAMPLE I

In this example, four control solutions were formulated. Two were made according to previous technology (viscosity modified with methyl cellulose) and two according to the present invention, polyvinyl acetate. Each pair was adjusted to glucose levels representing high and low control levels:

| Control | Ingredient | Amount |
| --- | --- | --- |
| Methyl Cellulose | water | 50 ml |
| | Gantrez AN-139 | 450 ml |
| | methyl cellulose | 5 g |
| | sodium benzoate | 1 g |
| | disodium EDTA (stabilizer) | 0.5 g |
| | glucose | 0.8 mg/ml - low |
| | | 3.0 mg/ml - high |
| Polyvinyl Acetate | water | 600 ml |
| | 43% solids polyvinyl acetate | 100 g |
| | copper pthalocyanine 3,4',4",4'''-tetrasulfonic acid tetrasodium salt | 52.5 mg |
| | Aerosil TM 200 | 700 mg |
| | sodium benzoate | 1400 mg |
| | disodium EDTA (stabilizer) | 700 mg |
| | Dow B (antifoamer) | 140 mg |
| | glucose | 0.4 mg/ml - low |
| | | 3.0 mg/ml - high |

The methyl cellulose had a molecular weight such that a 2% solution in water would have a viscosity of 4000 cp. Gantrez AN-139 comprises a 1.1% solution which is pre-hydrolyze by heating until clear, then adjusted to pH 6.7. The stabilizer and antifoamer are optional for performance of the control solutions.

Each solution was tested with a number of different glucose reagent strip lots (One Touch TM glucose reagent strips) in order to determine the representative precision of each solution with this reagent strip. Measurements were performed with a commercial glucose meter (One Touch TM glucose monitor) according to the Manufacturer's Instructions:

| Control | # lots | # replicates | glucose (mg/dl) | pooled Cv |
| --- | --- | --- | --- | --- |
| Methyl Cellulose | 20 | 15 | 80 | 6.5% |
| Methyl Cellulose | 20 | 15 | 300 | 7.2 |
| Polyvinyl Acetate | 259 | 10 | 40 | 2.01 |
| Polyvinyl Acetate | 259 | 5 | 300 | 3.22 |

As the reproducibility of measuring a solution on a given reagent strip lot gets better, the pooled Cv decreases. It can be seen from the above results that the controls made according to this invention gave lower pooled Cv's, and hence better precision, than the methyl cellulose controls.

It was determined that our control solution performs well on actual porous reagent membrane strips and glucose testing meters for glucose concentrations between 0 mg/dl glucose and 600 mg/dl. The control solution performs well on meters between 0 mg/dl glucose and 350 mg/dl glucose, or well within the desirable human blood sample range.

EXAMPLE II

As a demonstration of the ability of various different commercially available polymer suspensions to perform the flow control function described above, test strips were constructed according to FIG. 1, except that the matrix 11 was comprised of untreated 0.8 micron nylon membrane. Mixtures of various polymer suspensions with water were prepared and spotted onto the top of the strip, as with whole blood. After a 30 second penetration time, the diameter of the wetted area on the side 13 was measured to quantitate flow control due to the polymer particles. Since the hole 14 was 4.8 mm in diameter, a wetted area of 4.8 mm would be perfect flow control.

| Polymer Suspension | Polymer type | ratio of polymer suspension: water | diam. of wetted area (mm) |
| --- | --- | --- | --- |
| Union 76 Unocal 3016 | vinyl/ acrylic | 1:3 | 11 |
| | | 1:1 | 9 |
| | | 2:1 | 7 |
| | | 1:0 | 5.5 |
| Polidene 33-080 | chloride | 1:4 | 8 |
| | | 1:0 | 5.5 |
| Texigel 13-047 | acrylic | 1:0 | 6 |
| Borden Glu-All | vinyl | 1:15 | 10 |
| | | 1:3 | 6 |
| Scott Bader | carboxy- | 1:4 | 8 |
| Texigel 13-302 | lated acrylic | 1:0 | 6 |
| Air Products | vinyl | 7:1 | 9 |
| Airflex 400 | acetate/ethylene | 3:1 | 7 |
| | | 1:1 | 5 |

Although some polymer suspensions are more efficient than others in terms of controlling flow (i.e., achieve small wetted diameters with smaller amounts of polymer), all are capable of some degree of flow control. Thus, when a drop of this suspension is placed on the top side of the membrane, the flexible particles modify the flow of the aqueous medium into the membrane in a fashion similar to blood: the flexible particles deform to the shape of the membrane surface or pores, effectively sealing the pores. These particles may be comprised of any material flexible enough to deform to the shape of the surface or pores, while viscous enough to resist flow under the force of capillary action. Examples of such materials are polymers which are "tacky" at room temperature, viscous solutions of polymers, or viscous non-water soluble liquids such as oils.

The bulk viscosity of these controls is low, similar to blood, at the concentration of particles necessary to produce the desired flow control characteristics. Thus, these controls are easier to manufacture and dispense than viscosity-modified controls.

Therefore, this invention is useful in control solution verification for typical glucose testing monitors useful in combination with Porous reagent strips. It is to be understood that the invention is to be derived from the attached claims and their equivalents which follow.

What is claimed is:

1. A control solution which mimics whole blood, for use with a porous reagent strip comprising: a suspension of about 40% to about 55% solid polyvinyl acetate particles dispersed in water, and a dispersant to maintain said particles in suspension and glucose.

2. The solution of claim 1 wherein the dispersant is silicon dioxide.

3. The solution of claim 1 wherein the ratio of polyvinyl acetate suspension to water by weight is between 1:5 and 1:8.

4. The solution of claim 3 further comprising an offset adjusting dye for use with a reflectance measurement system.

5. The solution of claim 4 further comprising 0.0075% copper phthalocyanine tetrasulfonic acid tetrasodium salt.

6. The solution of claim 3 further comprising polyvinyl acetate having a particle size between 0.5 and 10 microns.

7. A control solution for use with a porous reagent strip having about 0.8 micron diameter pore size, said solution mimicking whole blood on said strip, comprising: a 40%-55% polyvinyl acetate suspension and water in a ratio of between 1:5 and 1:8 by weight, a dispersant to maintain said polyvinyl acetate in suspension and glucose.

8. The solution of claim 7 wherein the ratio of polyvinyl acetate suspension to water is about 1:6.

9. The solution of claim 8 further comprising 0.0075% copper phthalocyanine tetrasulfonic acid tetrasodium salt.

10. The solution of claim 8 wherein the dispersant is silicon dioxide.

11. The solution of claim 8 wherein the amount of solid polyvinyl acetate in the polymer suspension is between about 40% to about 55%.

* * * * *